United States Patent
Cooper et al.

(10) Patent No.: US 11,624,428 B2
(45) Date of Patent: Apr. 11, 2023

(54) LEVER ACTUATED GIMBAL PLATE

(71) Applicant: Intuitive Surgical Operations, Inc., Sunnyvale, CA (US)

(72) Inventors: Thomas G. Cooper, Menlo Park, CA (US); S. Christopher Anderson, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 17/569,378

(22) Filed: Jan. 5, 2022

(65) Prior Publication Data
US 2022/0128133 A1 Apr. 28, 2022

Related U.S. Application Data

(63) Continuation of application No. 16/780,432, filed on Feb. 3, 2020, now Pat. No. 11,248,686, which is a (Continued)

(51) Int. Cl.
*A61B 1/005* (2006.01)
*A61B 34/30* (2016.01)
(Continued)

(52) U.S. Cl.
CPC .......... *F16H 21/54* (2013.01); *A61B 1/0057* (2013.01); *A61B 34/30* (2016.02); *A61B 34/71* (2016.02);
(Continued)

(58) Field of Classification Search
CPC ..... B25J 9/06; B25J 9/065; B25J 9/106; B25J 9/104; B25J 9/1045; A61B 1/005;
(Continued)

(56) References Cited

U.S. PATENT DOCUMENTS

| 2,421,279 A | 5/1947 | Marty |
| 2,906,143 A | 9/1959 | Musser |

(Continued)

FOREIGN PATENT DOCUMENTS

| EP | 2548529 A1 | 1/2013 |
| EP | 2783643 A1 | 10/2014 |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

(Continued)

*Primary Examiner* — Bobby Rushing, Jr.

(57) ABSTRACT

A force transmission transmits forces received by three levers to an input gimbal plate having three support points. The input gimbal play may in turn transmit the force to a wrist assembly coupled to a surgical tool. The three axes of rotation for the three levers are parallel. Two of the levers may have half-cylinder surfaces at an end of the lever to receive a support point of the input gimbal plate. Two of the levers may be supported with one degree of rotational freedom orthogonal to the axis of rotation of the fulcrum. A spring may draw the second and third levers toward one another. Two levers may have stops that bear against the support points. The force transmission may include a parallelogram linkage that includes a rocker link pivotally coupled to the first lever and having a flat surface that supports the first gimbal support point.

20 Claims, 6 Drawing Sheets

Related U.S. Application Data continuation of application No. 14/461,320, filed on Aug. 15, 2014, now Pat. No. 10,550,918.

(60) Provisional application No. 61/866,238, filed on Aug. 15, 2013.

(51) Int. Cl.
| | |
|---|---|
| *F16H 21/54* | (2006.01) |
| *A61B 34/00* | (2016.01) |
| *B25J 9/10* | (2006.01) |
| *A61B 17/00* | (2006.01) |

(52) U.S. Cl.
CPC ............ *B25J 9/104* (2013.01); *B25J 9/106* (2013.01); *A61B 2017/00477* (2013.01); *A61B 2034/304* (2016.02); *A61B 2034/306* (2016.02); *Y10T 74/18712* (2015.01); *Y10T 74/20335* (2015.01)

(58) Field of Classification Search
CPC ....... A61B 1/0057; A61B 1/008; A61B 1/009; A61B 34/71; A61B 2034/301; A61B 2017/2939
See application file for complete search history.

(56) References Cited

U.S. PATENT DOCUMENTS

| | | |
|---|---|---|
| 3,312,496 A | 4/1967 | Albert et al. |
| 3,618,420 A | 11/1971 | Horwitt et al. |
| 4,139,104 A | 2/1979 | Mink |
| 4,243,257 A | 1/1981 | Shackleford |
| 4,540,211 A | 9/1985 | Masserang |
| 4,705,311 A | 11/1987 | Ragard |
| 4,728,137 A | 3/1988 | Hamed et al. |
| 4,751,821 A * | 6/1988 | Birchard .................. B25J 9/104 60/527 |
| 5,099,705 A | 3/1992 | Dravnieks |
| 5,317,952 A | 6/1994 | Immega |
| 5,325,845 A | 7/1994 | Adair |
| 5,792,135 A | 8/1998 | Madhani et al. |
| 5,807,377 A | 9/1998 | Madhani et al. |
| 5,816,769 A | 10/1998 | Bauer et al. |
| 5,855,583 A | 1/1999 | Wang et al. |
| 5,876,325 A | 3/1999 | Mizuno et al. |
| 6,322,312 B1 | 11/2001 | Sundar |
| 6,331,181 B1 | 12/2001 | Tierney et al. |
| 6,394,998 B1 | 5/2002 | Wallace et al. |
| 6,817,974 B2 | 11/2004 | Cooper et al. |
| 6,994,708 B2 | 2/2006 | Manzo |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,338,513 B2 | 3/2008 | Lee et al. |
| 7,608,083 B2 | 10/2009 | Lee et al. |
| 7,736,356 B2 | 6/2010 | Cooper et al. |
| 7,935,130 B2 | 5/2011 | Williams |
| 8,142,421 B2 | 3/2012 | Cooper et al. |
| 8,316,961 B2 | 11/2012 | Isobe et al. |
| 8,317,746 B2 * | 11/2012 | Sewell .................. A61B 34/30 604/95.04 |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,597,280 B2 | 12/2013 | Cooper et al. |
| 8,602,288 B2 | 12/2013 | Shelton, IV et al. |
| 8,603,077 B2 | 12/2013 | Cooper et al. |
| 8,771,270 B2 | 7/2014 | Burbank |
| 8,800,838 B2 | 8/2014 | Shelton, IV |
| 8,808,166 B2 | 8/2014 | Hosaka |
| 9,028,494 B2 | 5/2015 | Shelton, IV et al. |
| 9,078,684 B2 | 7/2015 | Williams |
| 9,204,923 B2 | 12/2015 | Manzo et al. |
| 9,232,979 B2 | 1/2016 | Parihar et al. |
| 9,243,696 B2 | 1/2016 | Isobe et al. |
| 9,259,274 B2 | 2/2016 | Prisco |
| 9,289,112 B2 | 3/2016 | Takemoto et al. |
| 9,533,122 B2 | 1/2017 | Weitzner |
| 9,664,262 B2 | 5/2017 | Donlon et al. |
| 9,839,439 B2 | 12/2017 | Cooper et al. |
| 9,913,694 B2 | 3/2018 | Brisson |
| 9,931,106 B2 | 4/2018 | Au et al. |
| 9,962,228 B2 | 5/2018 | Schuh et al. |
| 10,076,348 B2 | 9/2018 | Anderson et al. |
| 10,130,366 B2 | 11/2018 | Shelton, IV et al. |
| 10,550,918 B2 | 2/2020 | Cooper et al. |
| 10,682,141 B2 | 6/2020 | Moore et al. |
| 10,792,112 B2 | 10/2020 | Kokish et al. |
| 10,799,303 B2 | 10/2020 | Cooper et al. |
| 10,932,868 B2 | 3/2021 | Solomon et al. |
| 11,013,566 B2 | 5/2021 | Diel et al. |
| 2002/0111621 A1 | 8/2002 | Wallace et al. |
| 2002/0111635 A1 | 8/2002 | Jensen et al. |
| 2005/0042943 A1 | 2/2005 | Mocivnik et al. |
| 2005/0059960 A1 | 3/2005 | Simaan et al. |
| 2005/0119527 A1 | 6/2005 | Banik et al. |
| 2007/0043338 A1 | 2/2007 | Moll et al. |
| 2007/0232858 A1 | 10/2007 | Macnamara et al. |
| 2008/0046122 A1 | 2/2008 | Manzo et al. |
| 2008/0065102 A1 | 3/2008 | Cooper |
| 2008/0065105 A1 * | 3/2008 | Larkin .................. A61B 34/37 606/130 |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0088774 A1 | 4/2009 | Swarup et al. |
| 2009/0198272 A1 | 8/2009 | Kerver et al. |
| 2010/0170519 A1 | 7/2010 | Romo et al. |
| 2010/0175701 A1 | 7/2010 | Reis et al. |
| 2010/0198253 A1 | 8/2010 | Jinno et al. |
| 2010/0318101 A1 | 12/2010 | Choi et al. |
| 2011/0015648 A1 * | 1/2011 | Alvarez .................. A61B 34/76 606/130 |
| 2011/0015650 A1 | 1/2011 | Choi et al. |
| 2011/0071508 A1 * | 3/2011 | Duval ................ A61B 1/00087 606/1 |
| 2011/0118754 A1 | 5/2011 | Dachs, II et al. |
| 2011/0184241 A1 * | 7/2011 | Zubiate .................... B25J 9/104 600/141 |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0046522 A1 | 2/2012 | Naito |
| 2012/0123441 A1 * | 5/2012 | Au .......................... A61B 34/30 606/130 |
| 2012/0239060 A1 | 9/2012 | Orban, III et al. |
| 2012/0289974 A1 | 11/2012 | Rogers et al. |
| 2013/0046318 A1 | 2/2013 | Radgowski et al. |
| 2013/0123783 A1 | 5/2013 | Marczyk et al. |
| 2013/0144395 A1 | 6/2013 | Stefanchik et al. |
| 2013/0199327 A1 * | 8/2013 | Park ....................... F16C 11/04 403/121 |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0100558 A1 | 4/2014 | Schmitz et al. |
| 2014/0114327 A1 | 4/2014 | Boudreaux et al. |
| 2014/0257333 A1 | 9/2014 | Blumenkranz |
| 2014/0276723 A1 | 9/2014 | Parihar et al. |
| 2014/0309625 A1 | 10/2014 | Okamoto et al. |
| 2015/0051034 A1 | 2/2015 | Cooper et al. |
| 2015/0150635 A1 | 6/2015 | Kilroy et al. |
| 2015/0157355 A1 | 6/2015 | Price et al. |
| 2016/0058443 A1 | 3/2016 | Yates et al. |
| 2016/0151115 A1 | 6/2016 | Karguth et al. |
| 2016/0184034 A1 | 6/2016 | Holop et al. |
| 2016/0296219 A1 | 10/2016 | Srivastava et al. |
| 2016/0361049 A1 | 12/2016 | Dachs, II et al. |
| 2016/0361123 A1 | 12/2016 | Hares et al. |
| 2017/0007345 A1 | 1/2017 | Smith et al. |
| 2017/0022754 A1 | 1/2017 | Nien et al. |

(56) References Cited

U.S. PATENT DOCUMENTS

| | | |
|---|---|---|
| 2017/0027656 A1 | 2/2017 | Robert et al. |
| 2017/0172672 A1 | 6/2017 | Bailey et al. |
| 2017/0333037 A1 | 11/2017 | Wellman et al. |
| 2018/0168572 A1 | 6/2018 | Burbank |
| 2018/0229021 A1 | 8/2018 | Don et al. |
| 2019/0117325 A1 | 4/2019 | Kishi |
| 2019/0125468 A1 | 5/2019 | Adams |
| 2019/0223960 A1 | 7/2019 | Chaplin et al. |
| 2019/0231451 A1 | 8/2019 | Lambrecht et al. |
| 2019/0231464 A1 | 8/2019 | Wixey et al. |
| 2019/0239965 A1 | 8/2019 | Abbott |
| 2019/0249759 A1 | 8/2019 | Abbott |
| 2019/0298323 A1 | 10/2019 | Lambrecht et al. |
| 2019/0307522 A1 | 10/2019 | Lambrecht et al. |
| 2019/0328467 A1 | 10/2019 | Waterbury et al. |
| 2020/0173525 A1 | 6/2020 | Cooper et al. |
| 2021/0220062 A1 | 7/2021 | Lambrecht et al. |
| 2021/0372508 A1 | 12/2021 | Abbott |

FOREIGN PATENT DOCUMENTS

| | | |
|---|---|---|
| EP | 3103374 A1 | 12/2016 |
| EP | 3195993 A1 | 7/2017 |
| JP | H06114000 A | 4/1994 |
| JP | H10249777 A | 9/1998 |
| JP | 2003024336 A | 1/2003 |
| JP | 2004301275 A | 10/2004 |
| JP | 2005288590 A | 10/2005 |
| WO | WO-9729690 A1 | 8/1997 |
| WO | WO-0030557 A1 | 6/2000 |
| WO | WO-2009039506 A1 | 3/2009 |
| WO | WO-2012068156 A2 | 5/2012 |
| WO | WO-2015142290 A1 | 9/2015 |
| WO | WO-2016161449 A1 | 10/2016 |
| WO | WO-2016172299 A1 | 10/2016 |
| WO | WO-2016189284 A1 | 12/2016 |
| WO | WO-2017064303 A1 | 4/2017 |
| WO | WO-2017188851 A1 | 11/2017 |
| WO | WO-2018069679 A1 | 4/2018 |
| WO | WO-2020102776 A1 | 5/2020 |
| WO | WO-2020252184 A1 | 12/2020 |

OTHER PUBLICATIONS

Office Action for U.S. Appl. No. 16/780,432, dated Jul. 7, 2021.

* cited by examiner

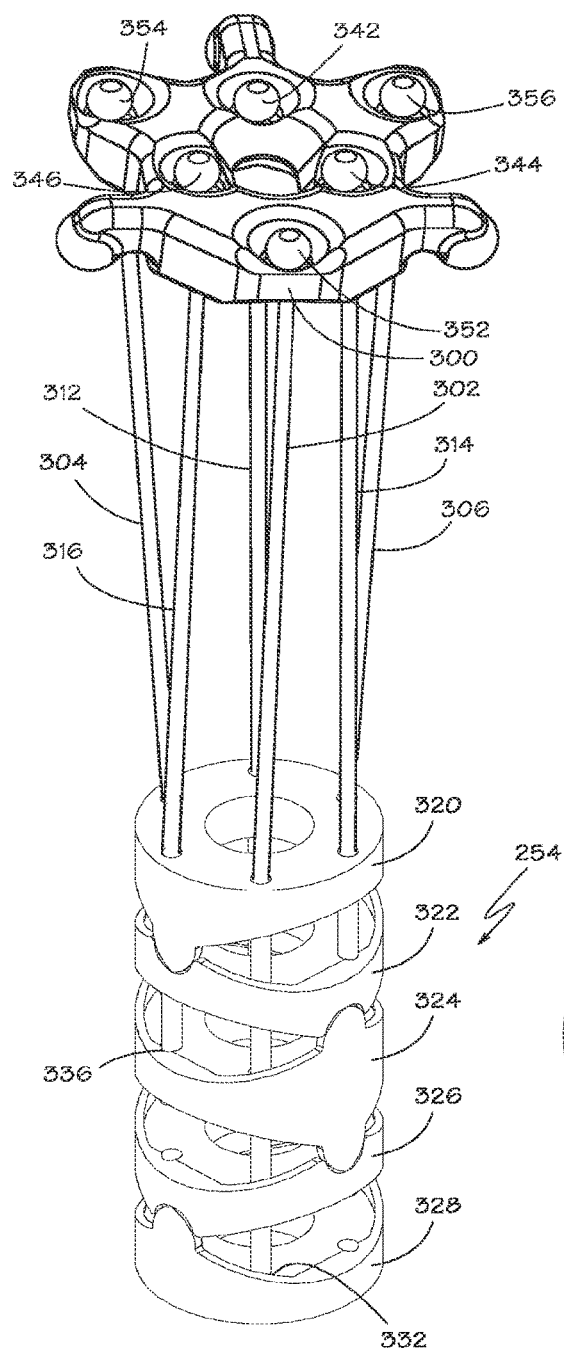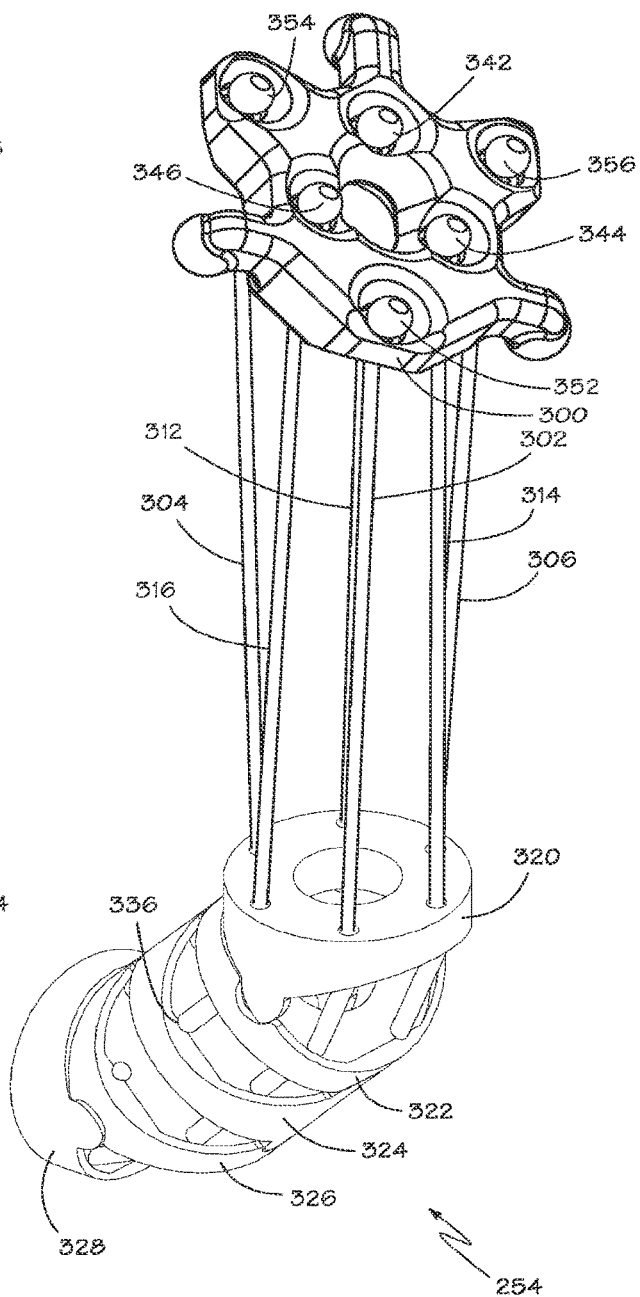
FIG. 3A
FIG. 3B

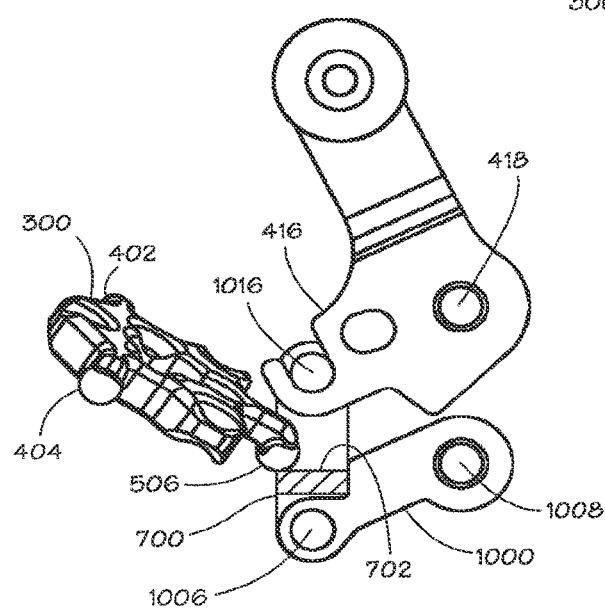
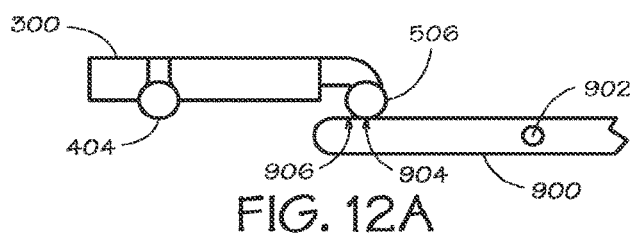
FIG. 12A
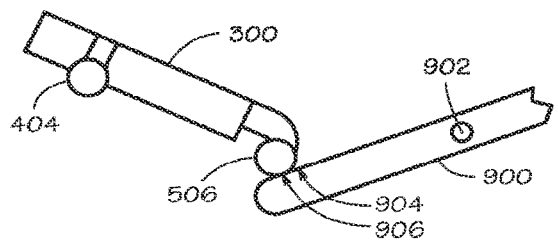
FIG. 12B
FIG. 13A
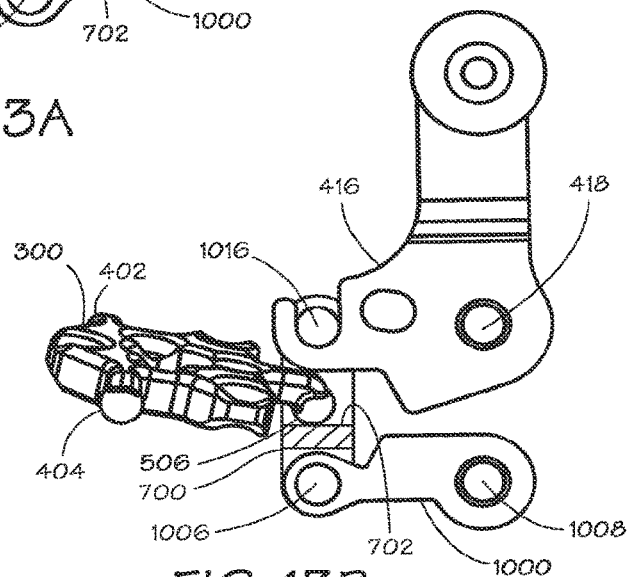
FIG. 13B
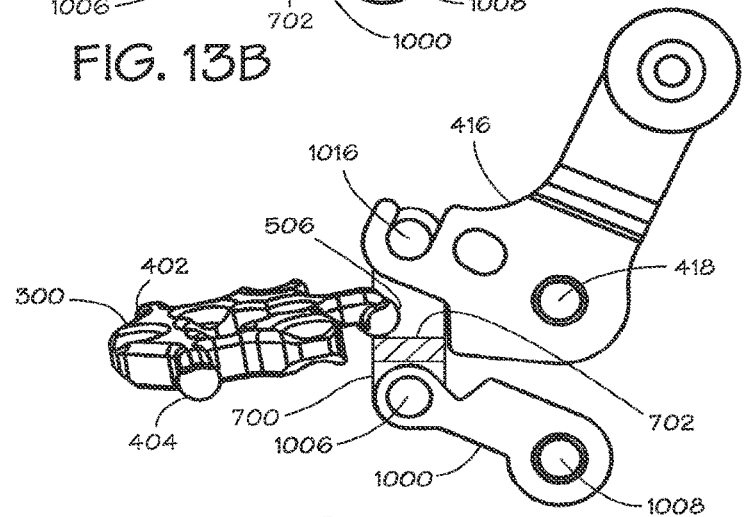
FIG. 13C

LEVER ACTUATED GIMBAL PLATE

CROSS REFERENCE TO RELATED APPLICATIONS

This application is a continuation of application Ser. No. 16/780,432 (filed Feb. 3, 2020), which is a continuation of application Ser. No. 14/461,320 (filed Aug. 15, 2014), which claims the benefit pursuant to 35 U.S.C. § 119(e) of U.S. Provisional Application No. 61/866,238 (filed Aug. 15, 2013), each of which is hereby incorporated by reference in its entirety.

BACKGROUND

Field

Embodiments of the invention relate to the field of force transmissions; and more specifically, to force transmissions for use in surgical instruments intended for use in minimally invasive surgeries.

Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a forceps, a scissors, a clamp, a needle grasper, or the like at one end of an elongate tube. The surgical tool is generally coupled to the elongate tube by one or more articulated sections to control the position and/or orientation of the surgical tool. An actuator that provides the actuating forces to control the articulated section is coupled to the other end of the elongate tube. A means of coupling the actuator forces to the articulated section runs through the elongate tube. The actuator may control an articulated section, such as a "wrist" the orients and manipulates the surgical tool, with means for coupling the actuator forces running through the elongate tube.

It may desirable that the elongate tube be somewhat flexible to allow the surgical instrument to adapt to the geometry of the surgical access path. In some cases, the articulated sections provide access to a surgical site that is not directly in line with the surgical access port. It may be desirable to use cables as the means of coupling the actuator forces to the articulated sections because of the flexibility they provide and because of the ability of a cable to transmit a significant force, a substantial distance, through a small cross-section. However, a cable is generally only able to transmit a force in tension. Thus it is generally necessary to provide two cables to transmit a bidirectional actuating force. The articulated section may be in the form of a gimbal that provides angular motion with two degrees of freedom around a center of rotation. A gimbal can be controlled by three cables.

If a wrist is to be provided with a wide range of motion, for example ±90°, it may be desirable to stack two gimbal joints and provide half of the motion in each of the two joints. This provides a more gradual change of direction at the wrist which may be advantageous if cables have to pass through the wrist to control the end effector. The two stacked sets of joints can be made to create a constant velocity joint that avoids the singularity or gimbal lock that occurs at 90° with one set of joints. It requires six cables to control two stacked gimbal joints. However, the six cables do not have independent motions.

In view of the above, it is desirable to provide an improved apparatus and method for transmitting actuating forces through an elongate tube of a surgical instrument intended for use in minimally invasive surgeries that uses six cables connected to two stacked gimbal type articulated sections.

SUMMARY

A force transmission transmits forces received by three levers to an input gimbal plate having three support points. The input gimbal play may in turn transmit the force to a wrist assembly coupled to a surgical tool. A first gimbal support point is supported by a first lever having a fulcrum with one degree of rotational freedom. Second and third gimbal support points may be supported by second and third levers having fulcrums with two degrees of rotational freedom. These fulcrums may include a first axle coupled to the lever and a second axle that supports the first axle and provides the fulcrum for the supported lever. A spring may draw the second and third levers toward one another. The force transmission may include a parallelogram linkage that includes a rocker link pivotally coupled to the first lever and having a flat surface that supports the first gimbal support point.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3A is a perspective view of a linkage mechanism for moving a wrist assembly in a first operative position.

FIG. 3B is a perspective view of the linkage mechanism of FIG. 3A in a second operative position.

FIG. 12A is a schematic elevation of a lever that could support a gimbal plate in a first operative position.

FIG. 12B is a schematic elevation of the lever of FIG. 12B in a second operative position.

FIG. 13A is elevation of a portion of the mechanism of FIG. 7 in a first operative position.

FIG. 13B is elevation of a portion of the mechanism of FIG. 7 in a second operative position.

FIG. 13C is elevation of a portion of the mechanism of FIG. 7 in a third operative position.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
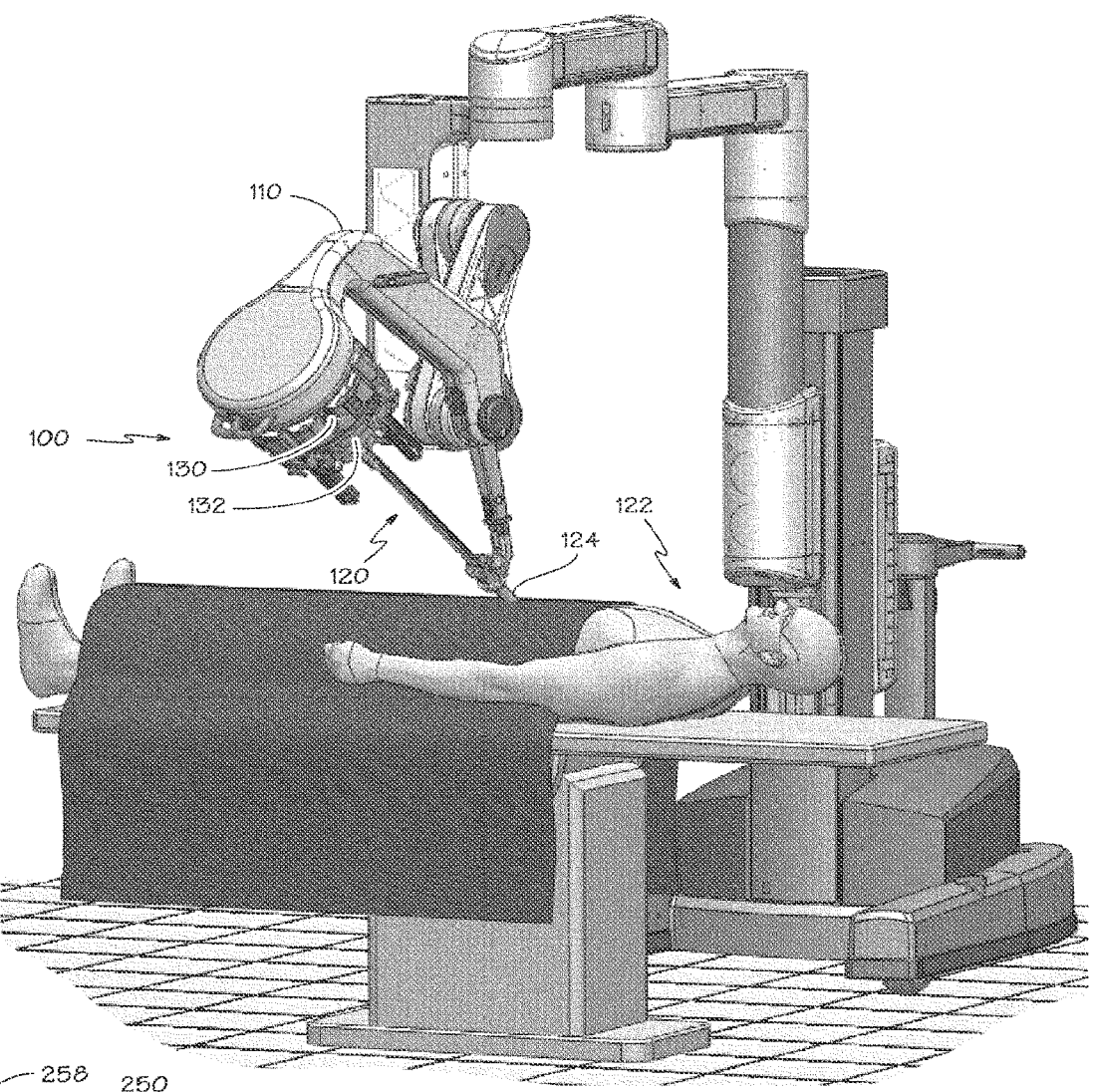
FIG. 1 is a simplified perspective view of a teleoperated surgical system with a mechanically actuated surgical instrument inserted through a port in a patient's abdomen.

FIG. 1 is a simplified diagrammatic perspective view of a teleoperated surgical system 100. The system 100 includes a support assembly 110 mounted to or near an operating table supporting a patient's body 122. The support assembly 110 supports one or more surgical instruments 120 that operate on a surgical site within the patient's body 122.

The term "instrument" is used herein to describe a device configured to be inserted into a patient's body and used to carry out surgical procedures. The instrument includes a surgical tool, such as a forceps, a needle driver, a shears, a monopolar cauterizer, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support for the surgical tool so that the position and orientation of the surgical tool can be manipulated.

The term "gimbal" is used herein to describe a device configured to provide a motion that is constrained to provide only rotation about two orthogonal axes. Typically such devices employ a Cardan suspension in which an innermost gimbal plate is supported by a rotational axis in an inner ring that is supported in turn by an orthogonal rotational axis in an outer ring. It will be observed that the gimbal plate is constrained so that it only moves rotationally about the center of motion at the point of intersection of the two rotational axes. It will also be observed that there is no net movement of any set of points that are equally spaced from the center of motion. For example, the sum of changes in position of three points that are spaced 120° apart on a circle centered on the center of motion will be zero for all positions of the gimbal plate.

The simplified perspective view of the system 100 shows only a single instrument 120 to allow aspects of the invention to be more clearly seen. A functional teleoperated surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional teleoperated surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control motors, such as servo motors, which, in turn, control the articulation of the surgical assembly. The forces generated by the motors are transferred via drivetrain mechanisms, which transmit the forces from the motors generated outside the patient's body 122 through an intermediate portion of the elongate surgical instrument 120 to a portion of the surgical instrument inside the patient's body 122 distal from the motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide 124, e.g., a cannula in the patient's abdomen. A functional teleoperated surgical system may provide an entry guide manipulator (not shown; in one illustrative aspect the entry guide manipulator is part of the support system 110) and an instrument manipulator (discussed below). The entry guide 124 is mounted onto the entry guide manipulator, which includes a mechanically actuated positioning system for positioning the distal end of the entry guide 124 at the desired target surgical site. The mechanically actuated positioning system may be provided in a variety of forms, such as a serial link arm having multiple degrees of freedom (e.g., six degrees of freedom) or a jointed arm that provides a remote center of motion (due to either hardware or software constraints) and which is positioned by one or more unpowered, lockable setup joints mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the mechanically actuated instrument manipulator 130. The mechanically actuated manipulator includes a coupler 132 to transfer controller motion from the mechanically actuated manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
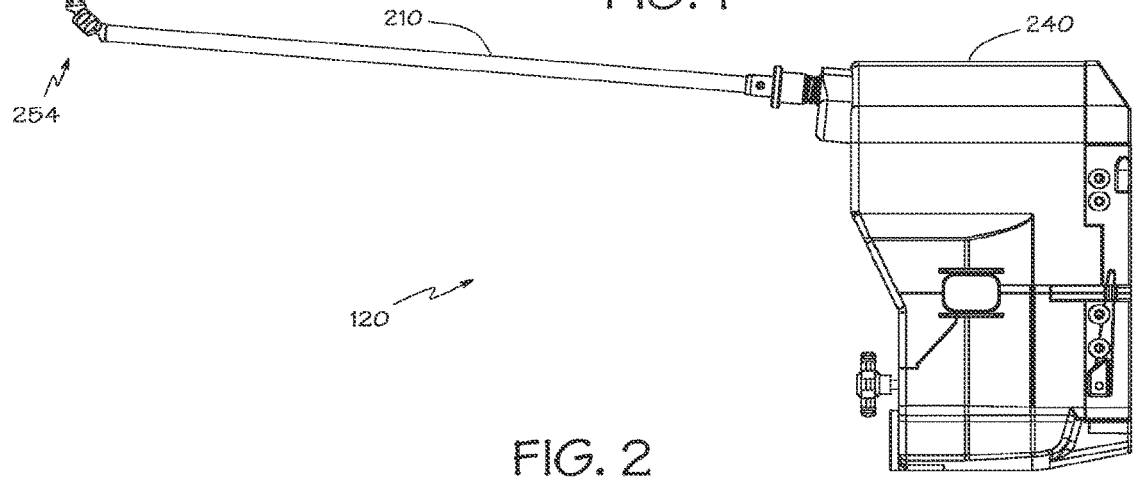
FIG. 2 is a plan view of a surgical instrument for use with a mechanically actuated manipulator.

FIG. 2 is a plan view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical devices such as the forceps 258 shown, a needle driver, a cautery device, a cutting tool, an imaging device (e.g., an endoscope or ultrasound probe), or a combined device that includes a combination of two or more various tools and imaging devices. In the embodiment shown, the surgical tool 258 is coupled to the elongate tube 210 by an articulated section in the form of a "wrist" 254 that allows the orientation of the surgical tool to be manipulated.

Surgical instruments that are used with the invention are controlled by a plurality of flexible cables. Cables provide a means of transmitting forces to the joints that is compact and flexible. A typical elongate tube 210 for a surgical instrument 120 is small, perhaps six millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale because forces and strengths of materials do not scale at the same rate as the size of the mechanisms. The cables must fit within the elongate tube 210 and be able to bend as they pass through the joints of the "wrist" 254.

FIGS. 3A and 3B are two perspective views showing a wrist assembly 254 and a linkage mechanism for moving the wrist assembly that could be used with the invention with the wrist assembly shown in two operative positions. The linkage mechanism transfers the forces applied on an input gimbal plate 300 in a proximal control mechanism to the articulated section 254 at the distal end of the elongate tube (not shown). In this embodiment, the articulated section 254 is a "wrist" that supports a surgical tool (not shown). The wrist 254 is coupled to the distal end of the elongate tube, which allows the wrist to be positioned adjacent the surgical site. Six cables 302, 304, 306, 312, 314, 316 couple the motion of the input gimbal plate 300 to the articulated section 254. It will be appreciated that the cables are not shown to scale and would normally be longer than shown.

The articulated section 254 in the embodiment shown includes five segments 320, 322, 324, 326, 328 that form a gimbal mechanism having two degrees of angular freedom. Each pair of adjacent segments (e.g. 320, 322) is coupled such that the two segments of the pair can rotate (e.g., pitch or yaw) relative to one other approximately around a single axis. (Each of the two segments may rotate about its own axis that is parallel to and slightly spaced apart from the axis of rotation for the other of the two segments.) Thus the two segments in each of the pairs of segments are not rotating relative to each other about a single axis but rather a pair of axes to provide a "cable balancing pivotal mechanism" as described in U.S. Pat. No. 7,736,356, FIG. 25, which is hereby incorporated in its entirety by reference. Three adjacent segments act as a gimbal plate because the two axes of the two pairs of segments are orthogonal to one another. The three segments 324, 326, 328 farthest from the distal end of the elongate tube act as an output gimbal plate. The first 324 of those three segments along with the two segments 322, 320 closest to the distal end act as a secondary output gimbal plate. Thus the wrist assembly has two degrees of rotational freedom.

The use of two stacked gimbals permits a greater range of angular movement and provides a greater radius of curvature for the articulation of the wrist. The stacked gimbals also allow singularity free motion in a manner similar to a double U-joint structure. A single U-joint contains single pair of orthogonal gimbal axes that intersect at a point. The single U-joint suffers from gimbal lock at 90 degree articulation, a condition in which the output can no longer roll. The secondary output gimbal plate moves to a first angle that is a portion of the total angle of the wrist movement and the output gimbal plate moves the remainder of the total angle. In the embodiment shown, the secondary output gimbal plate moves through one-half of the total angle and the output gimbal plate moves through the same amount relative to the secondary output gimbal plate to provide the total angle of movement.

Three output linkages 302, 304, 306, such as flexible cables, are coupled to the most distal segment 328 of the articulated section 254 at a first end 332 of the output linkages and coupled to the input gimbal plate 300 at a second end 352, 354, 356 of the output linkages. The three output linkages are coupled to the segment and to the gimbal plate with the three ends spaced apart so that they determine the position of a plane. The input gimbal plate 300 moves in response to movements of force inputs as described in detail below.

Each of three secondary output linkages 312, 316, 314 has a first end 336 coupled to the middle segment 324 of the articulated section 254, which is the most distal of the three segments 320, 322, 324 that act as a secondary output gimbal plate, and a second end 342, 344, 346 coupled to input gimbal plate 300. The three secondary output linkages are coupled to the segment and to the gimbal plate with the three ends spaced apart so that they determine the position of a plane.

Each secondary output linkage is coupled to the input gimbal plate 300 at a point that is diametrically opposite the point where an associated output linkage is coupled to the input gimbal plate and at half the radius of the associated output linkage. For example, the secondary output linkage designated by reference numeral 312 is associated with the output linkage designated by reference numeral 302.

The secondary output linkages 312, 316, 314 are coupled to the input gimbal plate 300 to move the secondary output linkages with a motion that is proportional to the motion of the associated output linkages 302, 304, 306. In the embodiment shown, each secondary output linkage moves one-half the distance of the associated output linkage in the opposite direction. The secondary output linkage is coupled to the secondary output gimbal plate 324 at a point that is diametrically opposite the point where the output linkage for the associated output linkage is coupled to the output gimbal plate 328. This causes the secondary output gimbal plate 324 to move through half the angle of the output gimbal plate 328. Both output gimbals move in the same direction because the diametrically opposed attachments cancel the effect of the opposite directions of motion at the input gimbal plate 300.

Figure 4:
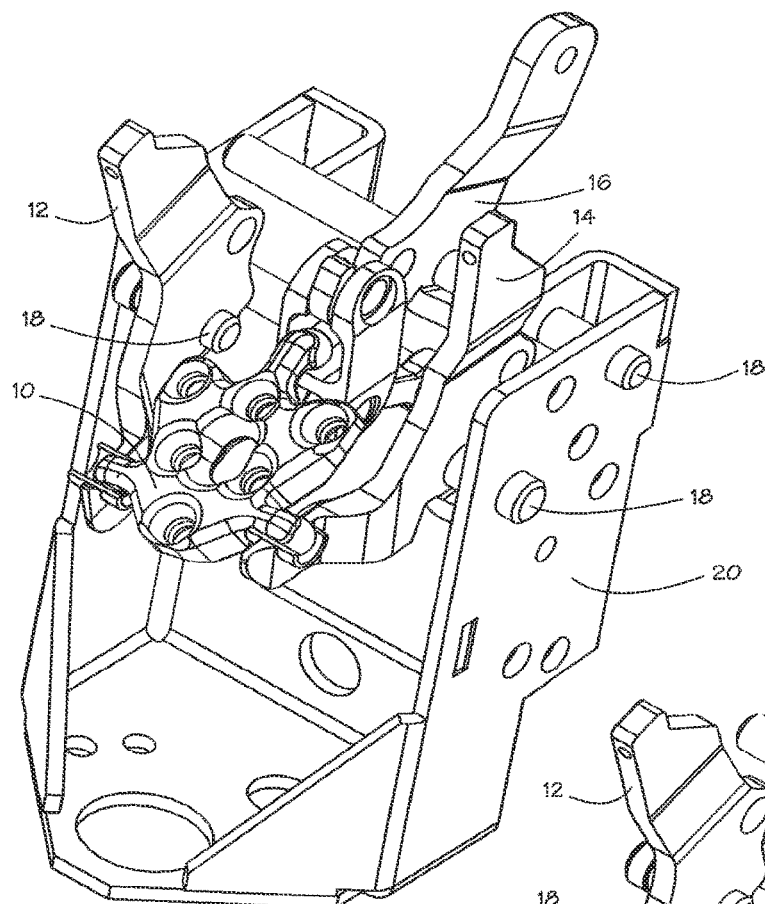
FIG. 4 is a perspective view of a mechanism for moving the linkage mechanism of FIG. 3A.

FIG. 4 is a perspective view of a mechanism for moving the input gimbal plate 10. Three levers 12, 14, 16 are provided to support the input gimbal plate 10. Each lever is rotatably supported by a fulcrum 18. The fulcrums are supported by a frame 20.

Figure 5:
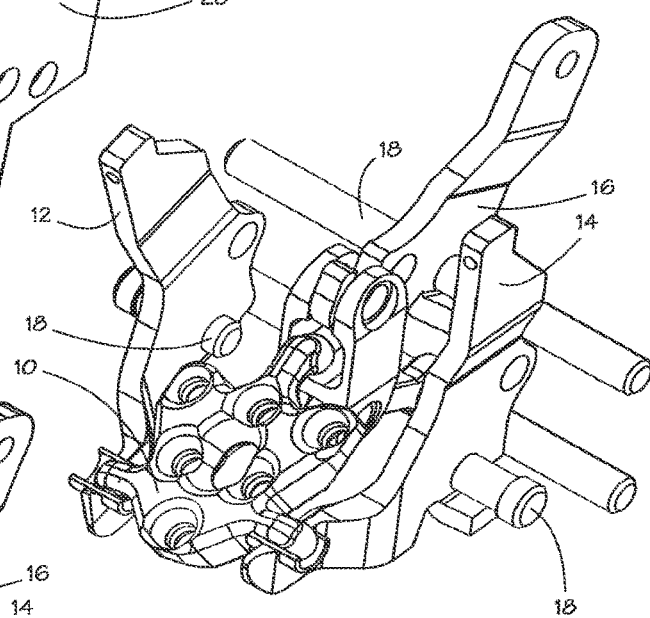
FIG. 5 is a perspective view of a portion of the mechanism of FIG. 4.
Figure 6:
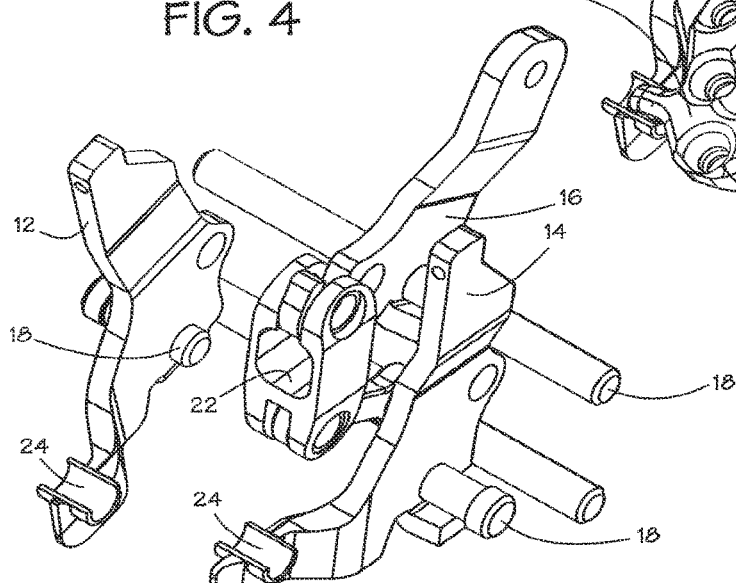
FIG. 6 is a perspective view of another portion of the mechanism of FIG. 4.

FIGS. 5 and 6 are perspective view of the mechanism shown in FIG. 4 for moving the input gimbal plate 10 with parts removed to allow certain aspects of the mechanism to be better seen. It will be appreciated that the distance between the ends of the levers changes as the levers are moved. The distance between the points on the gimbal plate 10 that are supported on the ends of the levers are fixed. Therefore it is necessary to provide a means to accommodate the fixed spacing of the support points on the gimbal plate 10.

As best seen in FIG. 6, two of the levers 12, 14 have half-cylinder surfaces 24 at the end of the levers to receive the support points of the gimbal plate 10. The axes of the half-cylinder surfaces 24 is parallel to the axes of the fulcrums 18. This maintains the support points of the gimbal plate 10 at a constant distance from the fulcrum 18 of the levers 12, 14 while allowing the support points to move along the axes of the half-cylinder surfaces 24 to accommodate the changing distance between the ends of the levers. The third lever 16 drives a parallelogram linkage 22 which is further explained in the description of the second embodiment below.

Figure 7:
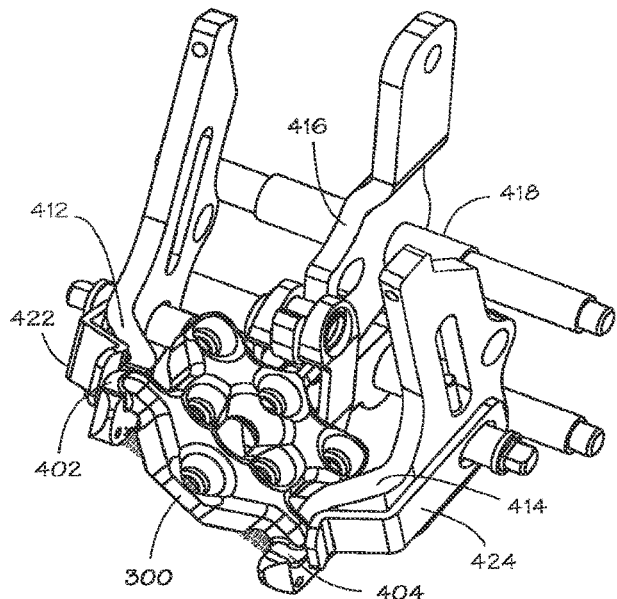
FIG. 7 is a perspective view of another mechanism for moving the linkage mechanism of FIG. 3A.

FIG. 7 is a perspective view of another mechanism for moving the input gimbal plate 300. Three levers 412, 414, 416 are provided to support the input gimbal plate 300.

Figure 8:
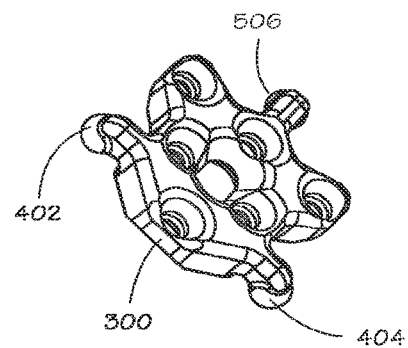
FIG. 8 is a perspective view of a portion of the mechanism of FIG. 7.

FIG. 8 is a perspective view of the input gimbal plate 300. The input gimbal plate 300 provides three support points 402, 404, 506. Each support point may be the center of a partial sphere. Each support point is supported by one of the three levers 412, 414, 416. A first lever 416 supports a first one of the three support points 506 of the input gimbal plate 300. A second lever 412 supports a second one of the three support points 402. A third lever 414 supports a third one of the three support points 404. The three support points 402, 404, 506 are equally spaced from the center of motion of the input gimbal plate 300. Therefore the input gimbal plate can be made to move as a gimbal plate with no displacement of the center of motion if there is no net displacement of the three support points 402, 404, 506.

In the embodiment shown two of the support points 402, 404 are equidistant from the axes of rotation for the levers. It will be appreciated that if these two support points 402, 404 are coupled to the levers 412, 414 such that the support points are constrained to have no displacement relative to the levers, then the levers must have a second degree of rotational freedom because the two support points move along a curved path.

Figure 9:
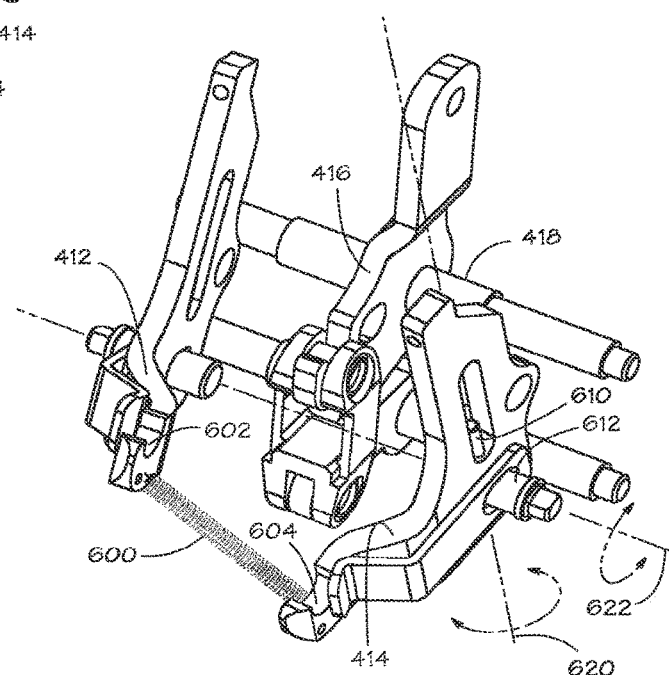
FIG. 9 is a perspective view of another portion of the mechanism of FIG. 7.
Figure 10:
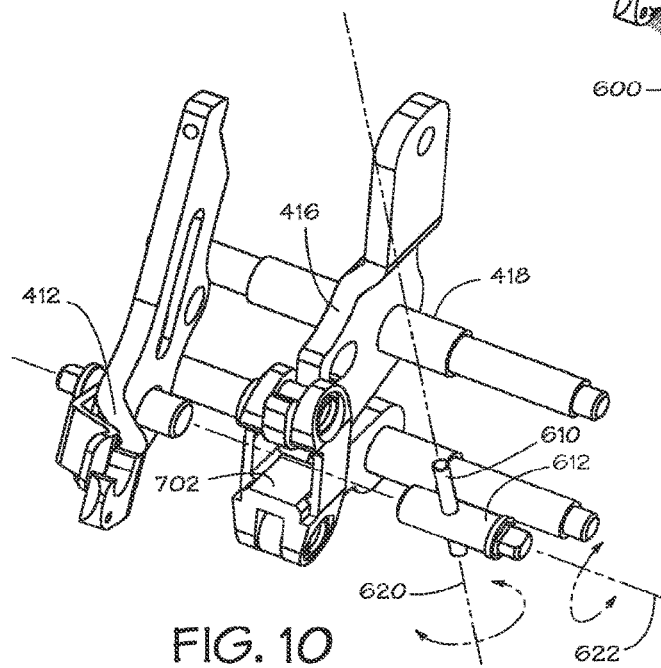
FIG. 10 is a perspective view of yet another portion of the mechanism of FIG. 7.

FIGS. 9 and 10 are perspective view of a mechanism shown in FIG. 7 for moving the input gimbal plate 300 with parts removed to allow certain aspects of the mechanism to be better seen.

Each of the second 412 and third 414 levers is supported by a fulcrum support that constrains the lever to two degrees of rotational freedom. In the embodiment best seen in FIG. 10, the lever 412 (FIG. 9) is rotatably supported by a first axle 610 that allows the lever to rotate about a first axis of rotation 620. The first axle 610 is in turn rotatably supported by a second axle 612 having a second axis of rotation 622 that is orthogonal to the first axis of rotation 620. The second axle 612 is the fulcrum for the lever. The first axle 610 allows the lever to follow the curved path of motion of the two support points 402, 404 of the input gimbal plate 300.

As seen in FIG. 9, the two outside levers 412, 414 are coupled by a spring 600 that provides an inward biasing force and draws the levers toward one another. The two outside levers 412, 414 provide receptacles 602, 604 that receive the two corresponding support points 402, 404. The receptacles 602, 604 are constructed so that the inward biasing force of the spring 600 couples the levers 412, 414 to the support points 402, 404 to provide only two degrees of rotational freedom for the support points and constrain the support points to have no displacement relative to the levers. A stop 422, 424 is provided on each of the second and third levers 412, 414 that bears against the second and third support points 402, 404 of the input gimbal plate 300 to limit movement of the levers toward one another.

Figure 11:
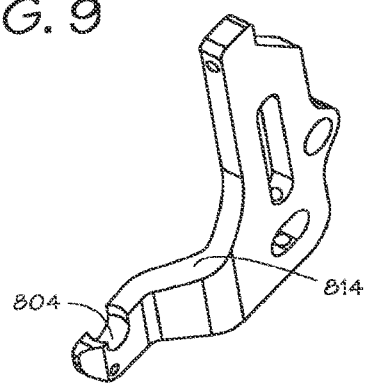
FIG. 11 is a perspective view of still another portion of the mechanism of FIG. 7.

FIG. 11 is a perspective view of another lever 814 that can be used in embodiments of the invention. This lever 814 provides a shaped receptacle 804 for a support point 404 of the input gimbal plate 300. The receptacle 804 is shaped so that the support point 404 of the input gimbal plate 300 can be engaged with or disengaged from the shaped receptacle 804 from the top of the lever 814. Once assembled the tension in the linkages attached to the input gimbal plate 300 hold the support point 404 of the gimbal plate in contact with the shaped receptacle 804. In this embodiment neither the spring nor the stops are required to prevent displacement of the support points relative to the levers. Providing the shaped receptacle in the second and third levers is sufficient to cause the levers to follow a curved path of motion of the second and third support points of the input gimbal plate.

FIGS. 12A and 12B are schematic elevations of a first lever 900 that supports the first one of the three support points 506 of the input gimbal plate 300. These figures illustrate an issue that arises if a simple coupling is used between the lever 900 and the support point 506. When the lever 900 is in a first position illustrated in FIG. 12A, the lever is coupled to the support point 506 at a first distance from the fulcrum 902 as indicated by reference numeral 904. When the lever 900 rotates to a second position illustrated in FIG. 12B, the gimbal plate 300 rotates about an axis that passes through the centers of the two other support points 402, 404 because of the constrained coupling of these support points to the second and third levers 412, 414 described above. As a result, the first lever 900 is coupled to the support point 506 at a second distance from the fulcrum 902 as indicated by reference numeral 906. This change in distance from the fulcrum 902 causes the support point 506 not to incorrectly track the displacements applied to the first lever 900.

FIGS. 13A, 13B, and 13C are elevations of a coupling between the first lever 416 that supports the first one of the three support points 506 of the input gimbal plate 300 that may be used to mitigate the issue of a changing distance from the fulcrum 418. A four-bar parallelogram linkage is formed with pivot points identified by reference numerals 418, 1016, 1006, and 1008. The portion of the first lever 416 between the lever's fulcrum 418 and the output 1016 forms the crank link of the four-bar linkage. The lever's fulcrum 418 and one of the pivot points 1008 are supported by the frame of the force transmission to form the fixed link of the four-bar linkage. A connecting rod 1000 is rotatably coupled to the fixed link at the pivot point 1008 opposite the pivot point that couples the crank link to the fixed link. A rocker link 700 is rotatably coupled to the crank link and the connecting rod 1000. The rocker link 700 provides a flat surface 702 that couples the first one of the three support points 506 of the input gimbal plate 300 to the first lever 416. The rocker link 700 is shown with a front portion cut away to allow the flat surface 702 to be seen. The parallelogram linkage causes the rocker link 700 to remain parallel to the fixed link. Therefore the displacement of the first lever 416 is transferred to the first one of the three support points 506 of the input gimbal plate 300 without the issues of changing distances from the lever's fulcrum point 418.

As seen in FIG. 3A, the second ends 352, 354, 356 of the output linkages 302, 304, 306 and the second ends 342, 344, 346 of the secondary output linkages 312, 316, 314 may include a termination that provides a spherical surface that is supported by a corresponding recess in the input gimbal plate 300. This may allow the second ends of the output linkages to swivel in the input gimbal plate.

Figure 14:
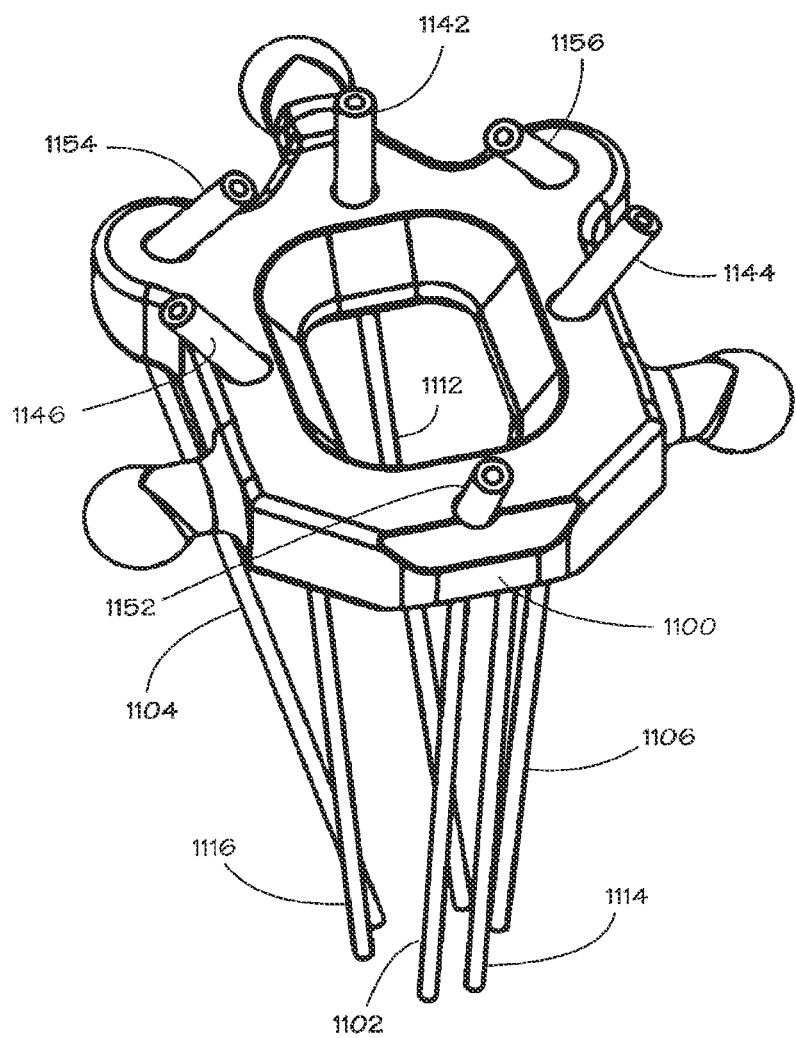
FIG. 14 shows another embodiment of the gimbal plate.

FIG. 14 shows another embodiment in which the second ends 1152, 1154, 1156 of the output linkages 1102, 1104, 1106 and the second ends 1142, 1144, 1146 of the secondary output linkages 1112, 1116, 1114 may include a terminations that are received in recesses in the input gimbal plate 1100 that do not allow the terminations to move in response to movements of the input gimbal plate. In this embodiment the output linkages may be formed of a flexible material, such as a stranded cable, that provides the necessary compliance at the second ends of the output linkages.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. For example, while first class bell crank levers have been shown as an exemplary embodiment, straight levers and levers of other classes may be used. The description is thus to be regarded as illustrative instead of limiting.

What is claimed is:

1. A medical instrument, comprising:
an elongate tube including a distal end portion and a proximal end portion;
a wrist assembly coupled to the distal end portion of the elongate tube;
a proximal control mechanism coupled to the proximal end portion of the elongate tube, the proximal control mechanism including an input member, the input member defining a center of motion;
a first output linkage routed along the elongate tube, the first output linkage having a distal end portion coupled to the wrist assembly and a proximal end portion coupled to the input member at a first position, the first position spaced apart from the center of motion by a first radial distance, the first position defining a movement of the distal end portion of the first output linkage based on an input from the input member; and
a second output linkage routed along the elongate tube, the second output linkage having a distal end portion coupled to the wrist assembly and a proximal end portion coupled to the input member at a second position, the second position spaced apart from the center of motion by a second radial distance that is less than the first radial distance, the second position defining a movement of the distal end portion of the second output linkage based on the input from the input member that is proportional to the movement of the distal end portion of the first output linkage.

2. The medical instrument of claim 1, wherein the wrist assembly includes:
a first wrist link; and
a second wrist link disposed between the first wrist link and the distal end portion of the elongate tube in a stacked configuration with the first wrist link, the stacked configuration having two degrees of rotational freedom.

3. The medical instrument of claim 2, wherein:
the first output linkage is coupled to the first wrist link of the wrist assembly; and
the second output linkage is coupled to the second wrist link.

4. The medical instrument of claim 3, wherein:
the second wrist link is rotatable to a first angle that is a portion of a total angle of wrist assembly movement; and
the first wrist link is rotatable a remainder of the total angle of wrist assembly movement.

5. The medical instrument of claim 1, wherein the proximal control mechanism includes a plurality of levers, the plurality of levers including:
a first lever that rotates about a first axis of rotation and supports a first support point of the input member;
a second lever that rotates about a second axis of rotation and supports a second support point of the input member; and
a third lever that rotates about a third axis of rotation and supports a third support point of the input member.

6. The medical instrument of claim 1, wherein the second radial distance is half the first radial distance.

7. The medical instrument of claim 1, wherein the first output linkage is a first cable and the second output linkage is a second cable.

8. The medical instrument of claim 1, wherein:
the distal end portion of the first output linkage moves a first distance based on the input from the proximal control mechanism; and
the distal end portion of the second output linkage moves a second distance based on the input from the proximal control mechanism, the second distance being less than the first distance.

9. The medical instrument of claim 1, wherein:
the input member is a passive element operated by an actuator of an instrument manipulator.

10. A medical instrument, comprising:
an input member supported within a proximal control mechanism, the input member defining a center of motion;
a first output linkage coupled to the input member at a first position, the first position spaced apart from the center of motion by a first radial distance, a distal end portion of the first output linkage configured to move by a first output distance in response to a movement of the input member, the first output distance being proportional to the first radial distance;
a second output linkage coupled to the input member at a second position, the second position spaced apart from the center of motion by a second radial distance that is less than the first radial distance, a distal end portion of the second output linkage configured to move a second output distance in response to the movement of the input member, the second output distance proportional to the second radial distance; and
a wrist assembly coupled to the distal end portion of the first output linkage and the distal end portion of the second output linkage, the wrist assembly including a plurality of wrist segments configured to articulate in response to the movement of the input member.

11. The medical instrument of claim 10, wherein:
the first output linkage is one of a first plurality of output linkages circumscribing the center of motion at the first radial distance; and
the second output linkage is one of a second plurality of output linkages circumscribing the center of motion at the second radial distance.

12. The medical instrument of claim 11, wherein:
the first plurality of output linkages includes three first output linkages; and
the second plurality of output linkages includes three second output linkages.

13. The medical instrument of claim 10, wherein:
the movement of the distal end portion of the second output linkage is proportional to and opposite the movement of the distal end portion of the first output linkage in response to the movement of the input member.

14. The medical instrument of claim 10, wherein:
the first output linkage is positioned diametrically opposite from the second output linkage relative to the center of motion.

15. The medical instrument of claim 10, wherein the second radial distance is half the first radial distance.

16. The medical instrument of claim 10, wherein the wrist assembly includes:
a first gimbal having three wrist segments of the plurality of wrist segments and two orthogonal axes of rotation; and
a second gimbal having three wrist segments of the plurality of wrist segments and two axes of rotation, the first gimbal and the second gimbal being arranged in a stacked configuration.

17. A medical instrument, comprising:
an elongate tube including a distal end portion and a proximal end portion;
a proximal control mechanism coupled to the proximal end portion of the elongate tube, the proximal control mechanism including an input member, the input member including a center of motion;
a first cable routed along the elongate tube, the first cable having a proximal end portion and a distal end portion, the proximal end portion of the first cable coupled to the input member at a first position spaced apart from the center of motion by a first radial distance;
a second cable routed along the elongate tube, the second cable having a proximal end portion and a distal end portion, the proximal end portion of the second cable coupled to the input member at a second position spaced apart from the center of motion by a second radial distance that is less than the first radial distance; and
a wrist assembly coupled to the distal end portion of the elongate tube, the wrist assembly including a distal wrist link, a proximal wrist link, and a central wrist link between the proximal wrist link and the distal wrist link, the distal end portion of the first cable coupled to the distal wrist link, the distal end portion of the second cable coupled to the central wrist link.

18. The medical instrument of claim 17, wherein:
a movement of the input member causes the distal end portion of the first cable to move a first distance and the distal end of the second cable to move a second distance that is less than the first distance.

19. The medical instrument of claim 18, wherein:
the second radial distance is half the first radial distance; and
the second distance is half the first distance.

20. The medical instrument of claim 17, wherein:
the proximal wrist link is rotatable relative to the central wrist link to a first angle that is a portion of a total angle of wrist assembly movement; and
the distal wrist link is rotatable relative to the central and link a remainder of the total angle of wrist assembly movement.

* * * * *